US012797492B2

(12) United States Patent
Chen et al.

(10) Patent No.: US 12,797,492 B2
(45) Date of Patent: Nov. 17, 2026

(54) POLYMER-MODIFIED MAGNETIC NANOMATERIAL, AND PREPARATION METHOD AND USE THEREOF

(71) Applicant: TONGJI UNIVERSITY, Shanghai (CN)

(72) Inventors: Bingdi Chen, Shanghai (CN); Wenjun Le, Shanghai (CN); Zheng Cui, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 469 days.

(21) Appl. No.: 18/561,599

(22) PCT Filed: Jun. 28, 2022

(86) PCT No.: PCT/CN2022/102012

§ 371 (c)(1),
(2) Date: Nov. 16, 2023

(87) PCT Pub. No.: WO2023/274252

PCT Pub. Date: Jan. 5, 2023

(65) Prior Publication Data

US 2024/0245808 A1 Jul. 25, 2024

(30) Foreign Application Priority Data

Jun. 30, 2021 (CN) ........................ 202110738850.1

(51) Int. Cl.
*A61K 49/00* (2006.01)
*C09K 11/02* (2006.01)
*C09K 11/06* (2006.01)

(52) U.S. Cl.
CPC ...... *A61K 49/0093* (2013.01); *A61K 49/0043* (2013.01); *C09K 11/02* (2013.01); *C09K 11/06* (2013.01); *C09K 2211/1007* (2013.01); *C09K 2211/1018* (2013.01)

(58) Field of Classification Search
None
See application file for complete search history.

(56) References Cited

U.S. PATENT DOCUMENTS

2010/0190006 A1 7/2010 Li et al.
2021/0163695 A1 * 6/2021 Wan .......................... B03C 1/01

FOREIGN PATENT DOCUMENTS

CN 106552600 4/2017
CN 107519501 12/2017
CN 108249429 7/2018

OTHER PUBLICATIONS

Chen et al.; Targeting Negative Surface Charges of Cancer Cells by Multifunctional Nanoprobes; IvySpring International Publisher; Theranostics 2016; 6(11): 1887-1898. doi: 10.7150/thno.16358 (Year: 2016).*
International Search Report issued in copending Chinese Patent Application No. PCT/CN2022/102012 on Sep. 6, 2022.
Chinese Office Action issued in codepending Chinese Patent Application No. 202210784391.5 on Jun. 25, 2023.
"Targeting Negative Surface Charges of Cancer Cells by Multifunctional Nanoprobes", pp. 1-12.

* cited by examiner

*Primary Examiner* — Robert A Wax
*Assistant Examiner* — John W Lippert, III
(74) *Attorney, Agent, or Firm* — Whiteford, Taylor & Preston LLP; Peter J. Davis

(57) ABSTRACT

Disclosed are a polymer-modified magnetic nanomaterial (polymer-modified MNM), and a preparation method and use thereof. Provided is the polymer-modified magnetic nanomaterial, including the following structure: a polymer is attached to or coated on a surface of a magnetic nanomaterial (MNM) to form the polymer-modified MNM that is positively charged, wherein the polymer is a cationic polymer, the MNM has a core-shell structure, a core is a magnetic nanoparticle (MNP), and a shell is a modified layer; and the modified layer is attached to or coated on a surface of the MNP to form a modified layer-compounded MNP; and a mass ratio of the polymer to the MNM in the polymer-modified MNM is in a range of 1:10 to 20:1.

11 Claims, 7 Drawing Sheets

Day 10

Day 20

Day 30

POLYMER-MODIFIED MAGNETIC NANOMATERIAL, AND PREPARATION METHOD AND USE THEREOF

This application is a national stage application of International Patent Application No. PCT/CN2022/102012, filed on Jun. 28, 2022, which claims priority to the Chinese Patent Application No. 2021107388501, filed on Jun. 30, 2021. The disclosure of the two patent applications are incorporated herein by reference in their entireties.

TECHNICAL FIELD

The present disclosure relates to a polymer-modified magnetic nanomaterial (MNM), and a preparation method and use thereof.

BACKGROUND

The incidence and mortality of cancer have been continuously increasing due to reasons such as population growth and aging as well as environmental concerns. Cancer is one of the major diseases leading to death in China and even in the world, and it has been difficult to obtain effective treatments for a long time. Therefore, research on cancer has long been an area of great interest to scientific and technological researchers around the world. Early diagnosis and treatment are extremely important for cancer patients to save their lives. Numerous studies are dedicated to the early diagnosis of cancer, and the early diagnosis and treatment make it possible to prolong the survival period of patients, increase the survival rate, and save the lives of patients.

Circulating tumor cells (CTCs) are widely considered to be a general term for various tumor cells that shed from the tumor site of patients with solid tumors and then enter the blood circulation system, and are also generally considered to be a main factor leading to cancer metastasis. The cancer metastasis constitutes the primary cause of death for most patients with cancer and an important factor for postoperative recurrence. Many studies have proved that treatments such as surgery and chemotherapy are also important factors that cause tumor cells to shed from the lesion and get into the bloodstream to form CTCs. The CTCs are considered to be the most potential multifunctional biomarkers, and have been found in many different types of cancers such as breast cancer, lung cancer, colon cancer, and even prostate cancer. The detection, counting, and correlation analysis of CTCs are of great significance to evaluate patients' conditions, and are expected to be applied to early detection, adjuvant therapy, efficacy evaluation, and prognosis estimation of tumors.

Currently, the reported methods for CTC enrichment mainly include physical approaches and biological approaches. For example, cell filters can be used to enrich CTCs, allowing small blood cells to pass through while entrapping large tumor cells; there is also antibody-dependent approaches that are based on the recognition of certain cell surface proteins, such as the capture of cancerous epithelial cells with an epithelial cell adhesion molecule (EpCAM). However, these methods are not based on the exclusive properties of tumor cells during the capture, resulting in false positives or false negatives in the detection, and are not broad-spectrum and cannot be widely used. Previous studies have found that tumor cells produce a large amount of lactic acid due to glycolysis, resulting in a large amount of negative surface charge, while normal cells are electrically neutral or slightly positively charged. Accordingly, efficient and selective enrichment of CTCs can be achieved based on the unique charge difference between tumor cells and normal cells, and has a broad spectrum. It is a key to entrap negatively charged CTCs by constructing high-performance positively charged nanomaterials.

Ferroferric oxide magnetic nanoparticles ($Fe_3O_4$ MNPs) have received extensive attention and research in the fields of biotechnology and medicine due to their special structure and excellent performance. Such materials are generally multifunctional composite nanoparticles with ferromagnetism, and are prepared by: coating a surface of an MNP prepared by a fairly mature method with an inorganic material such as silica or other organic polymer materials, and then subjecting the coated MNP to further reaction or surface modification. Such nanomaterials generally have characteristics such as easily controllable particle size and magnetic strength, having desirable biocompatibility and stability, and being easy to be modified. These characteristics greatly expand the application of the nanomaterials, such that these nanomaterials are researched and applied in many fields including drug targeted delivery, gene carrier, biomagnetic separation, magnetic hyperthermia, and magnetic resonance imaging. Based on the excellent physical and chemical properties of $Fe_3O_4$ nanoparticles, a simple and large-scale modification method can be developed for preparing these nanoparticles with desirable biocompatibility and positive surface charge. This method provides a high-quality nanoprobe for enrichment, detection, and guide treatment of the CTCs.

However, the nanomaterials reported in the prior art have deficiencies such as insufficient polymer content, poor stability, and long response time.

SUMMARY

A technical problem to be solved by the present disclosure is to overcome the disadvantages of insufficient polymer content, poor stability, and long response time of magnetic materials (positively charged magnetic nanoparticles, PCMNPs) in the prior art. The present disclosure provides a polymer-modified magnetic nanomaterial (MNM), and a preparation method and use thereof. In the present disclosure, the polymer-modified MNM has desirable stability and high response speed, and can achieve the enrichment of glycosylated proteins, polypeptides, nucleic acids, CTCs, and exosomes from complex samples with high selectivity, repeatability, and throughput. The polymer-modified MNM can also be applied to the preparation of a developer for in vivo fluorescence and magnetic resonance dual-modal imaging, or a photothermal therapeutic agent for cancer treatment.

The present disclosure solves the above technical problem with the following technical solutions:

The present disclosure provides a polymer-modified MNM, comprising the following structure:

- a polymer is attached to or coated on a surface of a MNM (that is, an outer layer of a shell, referred to as a coating) to form the polymer-modified MNM that is positively charged, wherein
- the polymer is a cationic polymer,
- the MNM has a core-shell structure, in which a core is a magnetic nanoparticle (MNP) (referred to as the core), and a shell is a modified layer; and the modified layer is attached to or coated on a surface of the MNP to form a modified layer-compounded MNP; and
- a mass ratio of the polymer to the MNM in the polymer-modified MNM is in a range of 1:10 to 20:1.

In an embodiment of the present disclosure, a mass ratio of the polymer to the MNM is in a range of 1:5 to 3:1, such as 1:3.

In an embodiment of the present disclosure, the polymer-modified MNM has a potential of +5 mV to +60 mV, such as +10 mV to +50 mV, and preferably +20 mV to +40 mV, such as +35 mV.

In an embodiment of the present disclosure, the MNM is a negatively-charged MNM, for example with a potential of −10 mV to −60 mV, such as −20 mV to −40 mV.

In an embodiment of the present disclosure, the polymer-modified MNM has a particle size of 10 nm to 600 nm, such as 300 nm to 500 nm and 350 nm to 400 nm.

In an embodiment of the present disclosure, the MNM has a particle size of 5 nm to 500 nm, such as 300 nm to 350 nm.

In an embodiment of the present disclosure, the shell has a thickness of 1 nm to 100 nm, such as 40 nm to 60 nm.

In an embodiment of the present disclosure, the MNP has a particle size of 5 nm to 500 nm, such as 250 nm to 300 nm.

In an embodiment of the present disclosure, the polymer is a (dendritic) branched polymer.

In an embodiment of the present disclosure, the polymer has a weight-average molecular weight (MW) of 2,000 to 300,000.

In an embodiment of the present disclosure, the polymer is a conventional cationic polymer in the art, such as one or more of polyethyleneimine (PEI), chitosan (β-chitosan), and polypyrrole.

In an embodiment of the present disclosure, the polymer can be: polyethyleneimine with a weight-average molecular weight of 2,000 to 100,000, such as 10,000, and a purity of 99%; β-chitosan with a weight-average molecular weight of 50,000 to 300,000, such as 50,000; and polypyrrole with a weight-average molecular weight of 5,000.

In the present disclosure, the MNP is a conventional MNP in the art, such as one or more of an oxide MNP (such as $Fe_3O_4$ and γ-$Fe_2O_3$), a metal MNP, a sulfide MNP, and a magnetic composite particle; preferably $Fe_3O_4$ MNP (hereinafter referred to as $Fe_3O_4$). The MNP can be prepared by conventional methods in the art, such as a solvothermal method and a co-precipitation method.

The MNP enables the polymer-modified MNM to have magnetism, and then move under the action of a magnet, such that the polymer-modified MNM can be used as a probe.

In the present disclosure, the MNM may be a conventional MNM in the art. The modified layer is wrapped on a surface of the MNP to form a composite MNM with a core-shell structure; a shell (layer) formed by the modified layer can not only prevent the aggregation of MNPs, but also prevent the MNPs from being destroyed, and can also conduct surface functionalization on the MNPs.

In an embodiment of the present disclosure, the modified layer can be prepared from a conventional organic and/or inorganic modified layer material in the art; for example, silica or fluorescently-labeled silica and/or surfactant-modified silica, such as the silica or the fluorescently-labeled silica. That is, the MNM can be a silica ($SiO_2$)-compounded MNP, or a fluorescently-labeled and/or surfactant-modified silica-compounded MNP.

In an embodiment of the present disclosure, when the MNM is a silica modified layer-compounded MNP, the silica modified layer-compounded MNP is a silica modified layer-compounded $Fe_3O_4$ MNP (hereinafter referred to as $Fe_3O_4@SiO_2$, namely ferroferric oxide/silica composite microspheres).

In an embodiment of the present disclosure, a surface of the modified layer (such as the silica modified layer) has amino groups obtained by modification, such that the modified layer provides a basis for reacting with a further modified (modified) substance. The modification can be conducted using conventional surface modifiers in the art; for example, modifying a surface of silica with amino group allows the silica to have a basis for amidation with a fluorescent dye having a carboxyl group. In the fluorescently-labeled silica-compounded MNP, a fluorescent dye is bonded to the silica-modified layer, for example, through amidation. In an embodiment, in the silica-compounded MNP, the surface of silica layer is modified with amino groups using a surface chemical modifier. The surface chemical modifier can be a conventional surface modifier capable of amino-modifying the surface of the silica-compounded MNP in the art; for example, ammonia water and/or 3-aminopropyltriethoxysilane (APTES), preferably ammonia water.

In an embodiment of the present disclosure, a mass ratio of the modified layer to the MNP is in a range of 50:1 to 1:10, such as 10:1.

In an embodiment of the present disclosure, the polymer-modified MNM has a stable duration of 2 years.

In an embodiment of the present disclosure, the polymer-modified MNM has a response time of 3 seconds to 2 min.

In an embodiment of the present disclosure, the MNM is a fluorescently-labeled silica-compounded MNP. A fluorescent dye (or fluorescent marker) in the fluorescently-labeled silica-compounded MNP can be a conventional fluorescent dye used in this type of material in the art, such as a fluorescent dye with a carboxyl group or capable of amidation with an amino group, such as fluorescein isothiocyanate (FITC) and/or a rhodamine dye, and/or a modified substance thereof. The fluorescent dye can be one or more of FITC, rhodamine B, rhodamine B 5-isothiocyanate (RBITC), and tetramethylrhodamine isothiocyanate (TRITC). A modifier can be APS-modified FITC and/or an APS-modified rhodamine dye. The APS may be 3-aminopropyltriethoxysilane (APTES) and/or 3-aminopropyltrimethylsilane (APTMS). For example, a modified substance of FITC can be APS-FITC (or called FITC-APS/APS-modified FITC); for another example, the fluorescent dye is APS-FITC.

The fluorescent dye (or fluorescent marker) in the fluorescent-labeled silica-compounded MNP is modified on the surface of silica-compounded nanoparticles in a conventional manner in the field, to form the fluorescent-labeled silica-compounded MNP; for example, the fluorescent dye is attached to the surface of the silica-compounded MNP through a connecting bond (eg, an amide bond). For example, the fluorescently-labeled silica-compounded MNP is APS-FITC-labeled $Fe_3O_4@SiO_2$. The silica modified layer-compounded MNP is a silica modified layer-compounded $Fe_3O_4$ MNP (hereinafter referred to as $Fe_3O_4@SiO_2$, namely ferroferric oxide/silica composite microspheres).

In an aspect of the present disclosure, the MNM may be a surfactant-modified silica-compounded MNP. A surfactant is one or a combination of two or more selected from the group consisting of sodium acetate, trisodium citrate, chitosan, polyvinylpyrrolidone, polyethylene terephthalate, stearic acid, gum arabic, hydroxypropyl methylcellulose, sodium alginate, lauryl sodium sulfate, sodium dodecylbenzene sulfonate, polyvinyl alcohol, a long-chain fatty acid, starch, and dodecanethiol. Through the modification of the surfactant, for example, the agglomeration of the formed nanoparticles can be avoided, thereby controlling a particle size of the polymer-modified MNM.

In an embodiment of the present disclosure, when the MNM is a fluorescently-labeled silica modified layer-compounded MNP (such as APS-FITC-labeled $Fe_3O_4@SiO_2$), a mass ratio of the silica-compounded MNP to the fluorescent dye (such as APS-FITC) is 20:1.

In an embodiment of the present disclosure, the polymer-modified MNM is PEI-modified APS-FITC-fluorescently-labeled $Fe_3O_4@SiO_2$; PEI has a weight-average molecular weight of 10,000 and a purity of 99%; and a mass ratio of PEI to the MNM is 1:3; and the polymer-modified MNM has a particle size of 20 nm to 500 nm and a potential of +10 mV to +60 mV.

In an embodiment of the present disclosure, the polymer-modified MNM is β-chitosan-modified APS-FITC-fluorescently-labeled $Fe_3O_4@SiO_2$ MNM; β-chitosan has a weight-average molecular weight of 50,000, and a mass ratio of β-chitosan to the MNM is 1:3; and the polymer-modified MNM has a particle size of 20 nm to 500 nm and a potential of +10 mV to +60 mV.

In an embodiment of the present disclosure, the polymer-modified MNM is polypyrrole-modified APS-FITC-fluorescently-labeled $Fe_3O_4@SiO_2$ MNM; polypyrrole has a weight-average molecular weight of 5,000, and a mass ratio of polypyrrole to the MNM is 1:3; and the polymer-modified MNM has a particle size of 20 nm to 500 nm and a potential of +10 mV to +60 mV.

The present disclosure further provides a method for preparing the polymer-modified MNM, including the following steps:

- subjecting an MNM and a mixture of a polymer and a solvent to modification to obtain the polymer-modified MNM; where the mixture of the polymer and the solvent is in an atomized form; and
- the polymer and MNM are those as defined in any technical solution of the polymer-modified MNMs described above.

In an embodiment of the present disclosure, in the mixture of the polymer and the solvent, the solvent can be a conventional solvent in this field, such as an alcoholic solvent; the alcoholic solvent can be methanol. A ratio of a mass of the polymer to a volume of the mixture of the polymer and the solvent may be a conventional mass-volume ratio in the art, for example, 5 mg:1 mL.

The atomized form of the mixture of the polymer and the solvent can be obtained by conventional methods in the art; for example, the atomized form is obtained by heating the mixture of the polymer and the solvent; preferably, the mixture of the polymer and the solvent is heated by a plasma method to obtain the atomized form.

The mixture of the polymer and the solvent is added at a volume flow rate of an atomized gas of 3 sccm to 5 sccm. (sccm is a volume flow unit, also known as a mass flow unit (Mass Flow), which means standard milliliters per minute: mL/min).

In some embodiments, the modification is conducted at a temperature of 100 °C to 300 °C, such as 200 °C.

In some embodiments, the modification is conducted in an inert atmosphere; and the inert atmosphere is provided by nitrogen and/or argon.

In some embodiments of the present disclosure, the modification is conducted, for example, by a plasma method. The plasma method can be conducted at conditions and operations as those of conventional plasma methods in the art. In some embodiments, the method includes the following steps: in an inert atmosphere with the presence of plasma glow, heating the mixture of the polymer and the solvent to obtain an atomized form, and subjecting the mixture and the MNM to modification to obtain the polymer-modified MNM.

In an embodiment of the present disclosure, the plasma glow is obtained by the following steps: in the inert atmosphere, adjusting a radio frequency power to generate the plasma glow in a plasma reaction chamber, where the inert atmosphere has a pressure of 300 Pa to 400 Pa, and the radio frequency power is 10 W±5 W. In some embodiments, a radio frequency power supply is preheated under vacuum, and then the inert atmosphere is introduced into the plasma reaction chamber; and the vacuum has a vacuum degree of less than or equal to 200 Pa, such as 150 Pa to 200 Pa.

In an embodiment of the present disclosure, the modification is conducted for 1 h to 2 h.

The MNM can be prepared by conventional preparation methods in the art. In some embodiments of the present disclosure, the method is as follows:

In an embodiment of the present disclosure, when the MNM is the silica ($SO_2$)— compounded MNP or the fluorescently-labeled silica-compounded MNP, and the silica-compounded MNP is $Fe_3O_4@SiO_2$, the MNM is prepared by a process comprising the following steps:

- step (a): in the presence of an alkaline reagent, adding a silicon reagent (also known as silane reagent) into a system of an $Fe_3O_4$ MNP and a solvent to obtain a mixture, and subjecting the mixture to modification to obtain $Fe_3O_4@SiO_2$; and/or
- step (b): subjecting $Fe_3O_4@SiO_2$ obtained in step (a) and a fluorescent dye to fluorescent labeling reaction in a mixture of a solvent and an alkaline reagent, to obtain the fluorescently-labeled silica-compounded MNP.

In some embodiments, the solvent in step (a) is selected from the group consisting of water and a mixture of water and an alcoholic solvent. In some embodiments, the alcoholic solvent is ethanol.

In some embodiments, the alkaline reagent is ammonia water.

In some embodiments, the silicon reagent is tetraethyl orthosilicate (TEOS) or tetramethyl orthosilicate (TMOS), such as TEOS.

In some embodiments, a ratio of a mass of the $Fe_3O_4$ MNP to a volume of the silicon reagent is 1500 g:1 L.

In some embodiments, the silicon reagent is used in a mixture with the solvent; for example, 2 mL of ethanol dissolves 100 μL of TEOS.

In some embodiments, the alkaline reagent is added in such an amount that the system of the $Fe_3O_4$ MNP and the solvent has a pH value of 9.5±0.5.

In some embodiments, the modification is conducted under ultrasound and/or mechanical stirring.

In some embodiments, the method further comprises a post-treatment in step (a); the post-treatment includes: after the modification is completed, washing the $Fe_3O_4@SiO_2$ obtained with assistance of magnetic separation; the washing is conducted with ethanol and deionized water separately, such as three times. In some embodiment, after the washing is completed, the $Fe_3O_4@SiO_2$ is dispersed in deionized water, and then prepared into a solution with a required concentration for later use, such as a solution with a concentration of 100 mg/mL.

In some embodiments, the solvent in step (b) is a mixture of an alcoholic solvent and water. In some embodiments, the water is deionized water. In some embodiments, the alcoholic solvent is ethanol. In some embodiments, a volume ratio of the alcoholic solvent to the water is in a range of 9:1 to 10:1, such as 9.7:1.

In some embodiments, a ratio of a mass of the silica-compounded MNP (such as $Fe_3O_4$@$SiO_2$) to a volume of the solvent is in a range of (0.56-0.6) g:1 L.

In some embodiments, the alkaline reagent is ammonia water. In some embodiments, a ratio of a mass of the silica-compounded MNP to a volume of the ammonia water is in a range of (42-45) g:1 L.

In some embodiments, the fluorescent dye is used in a mixture (such as a solution) with the solvent; the solvent in the solution is an alcoholic solvent, such as ethanol. In some embodiments, in the mixture of the fluorescent dye and the solvent, a ratio of a volume of the solvent to a mass of the fluorescent dye is 1.7 mL: 1 mg. For example, when the fluorescent dye is APS-FITC, the APS-FITC may be used in a form of a solution, such as an ethanol solution of APS-FITC, or 1.5 mg of FITC in 2.5 mL of ethanol.

In some embodiments, the fluorescent labeling reaction is conducted under ultrasound and mechanical stirring.

In some embodiments, the fluorescent labeling reaction is conducted in the dark.

In an embodiment of the present disclosure, the method further comprises adding the silicon reagent into the fluorescent labeling reaction (that is, a coating reaction is conducted while conducting the fluorescent labeling reaction). That is, further coating of silica is conducted at the same time. In some embodiments, a ratio of a mass of the silica-compounded MNP to a volume of the silicon reagent is 1000 g:1 L. In some embodiments, the silicon reagent is in a form of a mixture with the solvent; for example, a solution of TEOS in ethanol, and for another example, a mixture of 30 μL of TEOS in 1 mL of ethanol.

In an embodiment of the present disclosure, when the MNM is a fluorescently-labeled silica-compounded MNP, and the fluorescently-labeled silica-compounded MNP is an APS-FITC-fluorescently-labeled silica-compounded MNP (such as $Fe_3O_4$@$SiO_2$), the MNM is prepared by a process comprising the following steps: adding TEOS and APS-FITC in sequence into a mixed system of $Fe_3O_4$@$SiO_2$, a solvent, and ammonia water, and conducting reaction, to obtain the fluorescently-labeled silica-compounded MNP. In some embodiments, in the dark under ultrasound and mechanical stirring, TEOS is slowly added dropwise into the mixed system of $Fe_3O_4$@$SiO_2$, ethanol, and ammonia, and then a solution of APS-FITC is quickly added and the fluorescent labeling reaction is conducted.

In an embodiment of the present disclosure, the preparation method of the fluorescently-labeled silica-compounded MNP further includes a post-treatment. The post-treatment may be conducted with conventional operations and conditions in the art. In some embodiments, the post-treatment includes: after the fluorescent labeling reaction is completed, washing the MNP obtained with assistance of magnetic separation. In some embodiments, the washing is conducted with ethanol and deionized water separately, such as three times.

In an embodiment of the present disclosure, in the polymer-modified MNM, when the nanoparticles are labeled with a fluorescent dye of APS-FITC, the APS-FITC can be prepared by the following steps: adding APS into an ethanol solution of FITC, and conducting reaction to obtain the APS-FITC. In some embodiments, the reaction is conducted in the dark; the reaction is sufficiently conducted to obtain a clear solution, such as by mixing overnight for such as 8 h to 24 h. In some embodiments, a ratio of a mass of FITC to a volume of APS is 300 g:1 L.

In an embodiment of the present disclosure, the system of the $Fe_3O_4$ MNP and the solvent is prepared by the following steps: under ultrasound and mechanical stirring, washing $Fe_3O_4$ nano magnetic beads in the solvent with hydrochloric acid and deionized water successively until a resulting supernatant has a neutral pH value. In some embodiments, the hydrochloric acid has a mass concentration of 3.6% to 36%.

In an embodiment of the present disclosure, when the MNP in the MNM is $Fe_3O_4$, the MNP is prepared by the following steps: subjecting $FeCl_3 \cdot 6H_2O$ and an ethylene glycol solution of an alkali metal salt to reaction to obtain the $Fe_3O_4$ MNP.

In some embodiments, the alkali metal salt is trisodium citrate and/or NaAc.

In some embodiments, a molar ratio of $FeCl_3 \cdot 6H_2O$ to NaAc is 1:10.

In some embodiments, a ratio of a volume of the solvent to a molar number of $FeCl_3 \cdot 6H_2O$ is 10 L: 1 mol.

In some embodiments, the reaction is conducted at 200 °C.

In some embodiments, the reaction is conducted for 8 h.

In some embodiments, the preparation method of the $Fe_3O_4$ MNP further includes post-treatment. In some embodiments, the post-treatment includes: after the reaction is completed, washing the $Fe_3O_4$ MNP obtained with assistance of magnetic separation. In some embodiments, the washing is conducted with ethanol and deionized water separately, such as three times. In some embodiments, after the washing is completed, the $Fe_3O_4$ MNP is dispersed in deionized water to prepared into a solution with a required concentration for later use, such as a solution with a concentration of 100 mg/mL.

The present disclosure further provides a polymer-modified MNM, which is prepared by any one of the above preparation methods; and in some embodiments, the polymer-modified MNM is any one of the polymer-modified MNMs described above.

The present disclosure further provides use of a plasma method in preparation of a polymer-modified MNM, where the use includes the following steps: subjecting a mixture of a polymer and a solvent and an MNM to modification in the presence of plasma glow.

In some embodiments, the operations and conditions are the conditions and operations described in any one of the above polymer-modified MNMs. The polymer-modified MNM as well as the polymer and the MNM are those as described in any one of the above polymer-modified MNMs.

The present disclosure further provides use of the above polymer-modified MNM in enrichment and separation of a glycosylated protein, a polypeptide, a nucleic acid, a circulating tumor cell, and an exosome.

In an embodiment of the present disclosure, the use refers to use of the polymer-modified MNM in preparation of a developer for in vivo fluorescence and magnetic resonance dual-modal imaging (MRI), an electrochemical cell sensor, a drug and/or a medical product (reagent) for circulating tumor cell capture, or a photothermal therapeutic agent for cancer treatment. For example, the polymer-modified MNM is used for cell tracing, tumor tracing imaging, magnetic hyperthermia imaging, or blood vessel imaging.

In some embodiments, the (circulating) tumor cell is for example a folate receptor positive-tumor cell. In some embodiments, the tumor cell is one or more selected from the group consisting of: an ovarian cancer tumor cell, a cervical cancer tumor cell, a non-small cell lung cancer tumor cell, a colon cancer cell, a lung cancer cell, a rectal cancer cell, a gastric cancer cell, a breast cancer cell (triple-negative breast cancer tumor cell), an esophageal cancer cell, a liver cancer cell, and a leukemia cell; for example, the ovarian cancer tumor cell, the cervical cancer tumor cell, the triple negative breast cancer tumor cell, the colon cancer tumor cell, the non-small cell lung cancer tumor cell, and the leukemia cell.

In an embodiment of the present disclosure, the use is use of the polymer-modified MNM in preparation of a drug or a reagent for circulating tumor cell capture.

In some embodiments, a detection object of the drug or the reagent is a peripheral blood sample or a body fluid sample, where the body fluid may be urine, pleural fluid, ascites, and cerebrospinal fluid.

In some embodiments, the circulating tumor cell includes the ovarian cancer tumor cell, the cervical cancer tumor cell, the non-small cell lung cancer tumor cell, the colon cancer cell, the lung cancer cell, the rectal cancer cell, the gastric cancer cell, the breast cancer cell (triple-negative breast cancer tumor cell), the esophageal cancer cell, the liver cancer cell, or the leukemia cell.

In some embodiments, a process of capturing circulating tumor cells from a peripheral blood sample with the drug or the reagent includes the following steps:

- S1, subjecting the peripheral blood sample to density gradient centrifugation with a density gradient solution, collecting a buffy coat in a middle section, and removing plasma and red blood cells;
- S2, subjecting cells of the buffy coat to dilution and centrifugation, resuspending the cells to obtain a cell suspension, and removing proteins and impurities in the cell suspension;
- S3, activating the drug or the reagent by ultrasound, mixing the activated drug or reagent with the cell suspension obtained in S2 at a volume ratio of 3:100, and conducting adsorption;
- S4, subjecting a drug or a reagent obtained in S3 after adsorbing the cell suspension to magnetic field separation, enriching circulating tumor cells, and then subjecting the circulating tumor cells to resuspending, centrifuging, and Diff-Quik staining; and
- S5, observing the circulating tumor cell under a microscope, and conducting identification and counting according to tumor morphology.

In some embodiments, in S1, before conducting the density gradient centrifugation, the peripheral blood sample is diluted 3 to 4 times with phosphate buffer saline (PBS).

In some embodiments, the adsorption in S3 and the magnetic field separation and the enriching in S4 each are conducted at a temperature of 4 °C.

In some embodiments, the polymer-modified MNM includes: an MNP core, a shell of a modified layer, and a coating of a cationic polymer, where the polymer is attached to or coated on a surface of the MNM to form a positively-charged polymer-modified MNM; the MNM is a core-shell structure, where a core is the MNP, and a shell is the modified layer; the modified layer is attached to or coated on a surface of the MNP to form a modified layer-compounded MNP. In some embodiments, a mass ratio of the polymer to the MNM in the polymer-modified MNM is in a range of 1:10 to 20:1.

TERMS

"Deionized water" means pure water from which impurities in the form of ions have been removed. ISO/TC 147 of the International Organization for Standardization defines "deionization" as: deionized water is completely or incompletely removed from ionized species.

On the basis of conforming to common knowledge in the art, the above-mentioned preferred conditions can be combined arbitrarily to obtain preferred embodiments of the present disclosure.

The reagents and raw materials used in the present disclosure are all commercially available.

The present disclosure has the following positive progress effects:

(1) Conventional surface modification methods (such as surface coating, surface oxidation, high-energy ray treatment, and surface grafting modification) have defects such as surface structure damage, uncontrollable shape and thickness, disappearance of material surface original properties, and complicated post-treatment. Surface modification by gas-phase radical polymerization can avoid these defects, but also shows disadvantages such as small polymer concentration, vacuum conditions, and long polymerization time. As an improved method of the gas phase polymerization, the present disclosure proposes a concept of atomized polymerization modification. That is, after a polymer is dissolved in an organic solvent, a resulting polymer solution is atomized to form a mist-like polymer droplet that condenses on a plasma-treated surface and reacts to realize the surface modification of the polymer material. The atomized polymerization modification is mainly initiated by plasma treatment of the surface to prepare a polymer material with a special surface morphology. PEI, chitosan, and polypyrrole are used as substrates. After plasma treatment, the polymerization of atomized polymers on a surface of the substrate is initiated to improve the surface properties of the materials.

(2) In the present disclosure, the polymer-modified MNM can be used in the detection of CTCs, specifically the preparation of a drug or reagent for capturing the CTCs in peripheral blood, and a detection object is a peripheral blood sample. Compared with the prior art, the present disclosure has one or more of the following advantages: (1) new use of the polymer-modified MNM has high sensitivity, excellent detection rate, and desirable specificity, and captured CTCs are active and can be used for follow-up research; (2) compared with existing CTC detection methods, the new use shows advantages of less blood sample requirement, rapid detection, and easy operation; (3) the new use has a low single detection cost, and only needs to be equipped with a microscope and a magnetic separator, thereby reducing medical burden; and (4) the new use is applicable to multiple scenarios such as curative effect evaluation, recurrence warning, and prognosis value achievement of tumor patients, and provides references for doctors during medication and treatment.

BRIEF DESCRIPTION OF THE DRAWINGS

FIG. 1A shows the potential characterizations, which correspond to $Fe_3O_4@SiO_2$, PEI positive electromagnetic beads, plasma polymerization-based PEI positive electromagnetic beads, chitosan positive electromagnetic beads, plasma polymerization-based chitosan positive electromagnetic beads, polypyrrole positive electromagnetic beads, and plasma polymerization-based polypyrrole positive electromagnetic beads; and FIG. 1B shows the fluorescence spectra.

FIG. 3A represents before the magnetic separation, FIG. 3B represents after the magnetic separation.

FIG. 5A shows potential comparison, and FIG. 5B shows particle size comparison.

DETAILED DESCRIPTION OF THE EMBODIMENTS

Figure 1A:
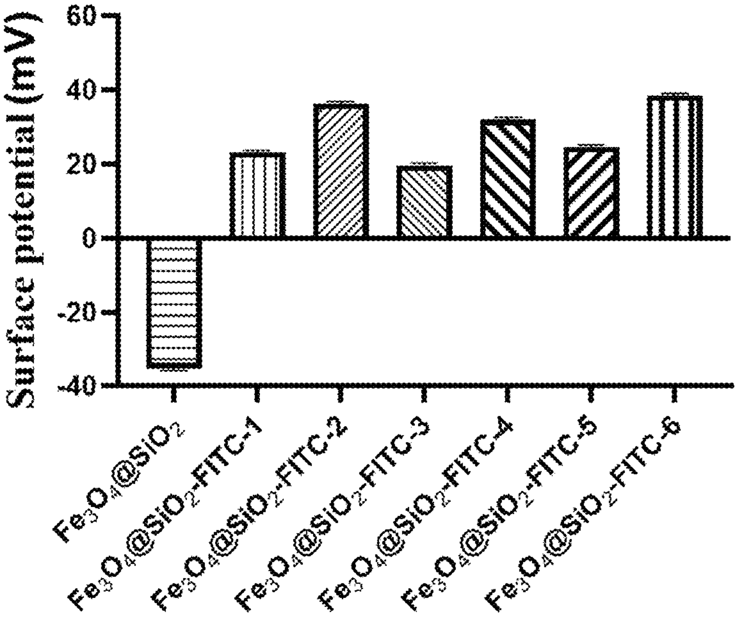
FIGS. 1A and 1B show potential characterizations and fluorescence spectra of various nanomaterials according to Examples 1 to 7, where

The present disclosure is further described below with references to examples, but the present disclosure is not limited to the scope of the described examples. The experimental methods in the following examples which are not elaborated with specific conditions are conducted according to conventional conditions or according to product instructions.

A flow rate unit standard cubic centimeter per minute (sccm) represents standard milliliters per minute.

Experimental Reagents

Ferric chloride ($FeCl_3 \cdot 6H_2O$), ammonia water ($NH_3 \cdot H_2O$), concentrated hydrochloric acid (HCl, 37%), and absolute ethanol were purchased from Sinopharm Group, China. Tetraethyl orthosilicate (TEOS), sodium acetate (NaAc), ethylene glycol (EG), 3-aminopolyethyleneimine (PEI) (MW=10,000), β-chitosan (MW=5,000), polypyrrole (MW=50,000), 3-aminopropyltriethoxysilane ((3-aminopropyl)triethoxysilane, APTES), and fluorescein isothiocyanate (FITC) were purchased from Sigma Aldrich. Deionized water (DIW, 18.2 MΩ·cm) used in the experiment were self-made by a Thermo Easypure II UF pure water preparation system in the laboratory.

Main Experimental Instruments and Equipment

TABLE 1

| Experimental Instruments and Equipment | | |
|---|---|---|
| Instruments and equipment | Model | Manufacturer |
| Electronic analytical balance | BS 124 S | Sartorius, Germany |
| Nanolaser particle size analyzer | NanoZS90 | Malvern, UK |
| Spectrophotometer | LS-55 | PerkinElmer, USA |
| Far infrared dryer | WS70-1 | Shanghai Hualian Medical Devices Co., Ltd., China |
| High-temperature oven | ST-120B2 | Shanghai Espec Equipment Co., Ltd., China |
| Ultrasonic cleaner | KQ-400KDE | Kunshan Ultrasonic Instrument Co., Ltd., China |
| Constant-temperature water bath | 501-type | Shanghai Pudong Rong-feng Scientific Instrument Company, Ltd., China |
| Ultrapure water purifier | Easypure II UF | Thermo, USA |
| Electric stirrer | D2010W | Shanghai Meiyingpu Instrument Manufacturing Co., Ltd., China |
| Field emission SEM | S-4800 | Hitachi, Japan |
| TEM | JEM-2100 | JEOL, Japan |

Example 1 Preparation of Multifunctional MNM (1) Preparation of Superparamagnetic Ferroferric Oxide Nanoparticles Solvothermal preparation of ferroferric oxide nanoparticles: 0.81 g of ferric chloride hexahydrate ($FeCl_3$ $6H_2O$, 0.003 mol) and 2.56 g of anhydrous sodium acetate (NaAc, 0.03 mol) were accurately weighted and magnetically stirred for 30 min to dissolve completely in 30 mL of ethylene glycol (PEG), to obtain a brown-yellow mixed solution. The mixed solution was transferred into a stainless steel reactor resistant to high temperature and high pressure, and placed in a high-temperature oven, then a reaction was conducted at a constant temperature of 200 °C for 8 h. After the reaction was over, the reactor was taken out and cooled to ambient temperature quickly with running water to obtain a reaction solution. A reaction product was separated from the reaction solution by magnetic adsorption, the remaining reaction solution was removed, and the reaction product was washed three times with ethanol and deionized water separately under the conditions of magnet-assisted separation to obtain a black product. The black product was re-diluted and dispersed in deionized water, and prepared to a ferroferric oxide dispersed solution in deionizer water with a rough concentration of 100 mg/mL according to a rough estimate, and a relatively accurate concentration was measured by a solid content determination method, and marked. In the end, the ferroferric oxide dispersed solution was stored uniformly.

(2) Preparation of Ferroferric Oxide/Silica Composite Microspheres

Treatment of the ferroferric oxide nanoparticles with HCl: 1 mL of concentrated hydrochloric acid with a mass concentration of 36% was added to 9 mL of the ferroferric oxide dispersed solution in deionized water, and stirred under ultrasound in a round bottom flask for 10 min to 15 min (at 30 °C to 40 °C and a power of 80 W to 120 W), the aqueous solution was removed by magnetic separation, the remaining ferroferric oxide was washed 6 to 7 times with deionized water until a pH value of a supernatant was neutral. 83.8 g of ethanol and 25.7 g of deionized water were added into a three-necked flask, 150 mg of ferroferric oxide nano magnetic beads washed with hydrochloric acid and deionized water were added thereto, and mechanically stirred under ultrasound for about 15 min (at 30 °C to 40 °C and a power of 80 W to 120 W), ammonia water was added to adjust the pH value to about 9.5, and 100 μL of TEOS was dissolved in 2 mL of ethanol and added to continue the above reaction, mechanically stirred for another 12 h. A product was obtained by magnetic separation and washed three times with absolute ethanol and deionized water with the assistance of magnetic separation. An obtained washed product was dispersed in deionized water, and prepared to a ferroferric oxide/silica composite microspheres dispersed solution with a rough concentration of 100 mg/mL according to a rough estimate, and a relatively accurate concentration was measured by a solid content determination method and marked, and the ferroferric oxide/silica composite microspheres dispersed solution was stored at room temperature.

Example 2 Preparation of PEI Positive Electromagnetic Beads (1) Preparation of APS-FITC 1.5 mg of FITC dye was dissolved in 0.5 mL of absolute ethanol in a 1.5 mL centrifuge tube. The resulting FITC solution was transferred into a small glass reaction vial, diluted with 2 mL of absolute ethanol, and magnetically stirred for 1 min to mix well. 5 μL of APS was added into the resulting diluted solution, the reaction system immediately turned orange, and then magnetically stirred overnight until a product became a clear solution, thereby obtaining an APS-FITC solution, where the experiment was conducted always in the dark.

(2) Preparation of Fluorescent Negative Electromagnetic Beads by Fluorescence Labeling and TEOS Coating 0.7 mL of ammonia water was added into a mixture of 45 mL of absolute ethanol and 5 mL of deionized water, and mechanically stirred to mix well. 30 mg of $Fe_3O_4@SiO_2$ prepared according to Example 1 was added and stirred under ultrasound for about 30 min to obtain a uniform dispersion. 30 μL of TEOS was dissolved in 1 mL of absolute ethanol, and added into the above dispersion slowly dropwise under ultrasound and mechanical stirring to obtain a reaction system. The reaction system was stirred under ultrasound for another 15 min, then an APS-FITC solution was quickly added into the reaction system, and mechanically stirred under ultrasound for another 4 h in the dark. Then the ultrasound was stopped, the reaction system was mechanically stirred for 18 h, and a product was obtained under the assistance of magnetic separation and washed three times with ethanol and deionized water separately, obtaining the fluorescent negative electromagnetic beads, which were marked as "fluorescent negative electromagnetic beads-production date", a concentration was calculated and marked, and the beads were prepared into a 10 mg/mL dispersion, which was stored according to different categories in a refrigerator at 4 °C in the dark.

(3) Preparation of PEI-Modified Fluorescent Positive Electromagnetic Beads 25 mL of methanol was added to 18 mg of the fluorescent negative electromagnetic beads obtained in the previous step, and mechanically stirred under ultrasound for 10 min in the dark until a mixture is uniform to obtain a reaction solution. 10 mg of PEI (MW=10,000, 99%, purchased from Aladdin) was dissolved in 2 mL of methanol, added to the above reaction solution, stirred under ultrasound for 2 h. The resulting solution was subjected to magnetical separation to obtain a product, which was washed once with methanol and three times with water. Sample treatment: an obtained aqueous dispersion was marked as "fluorescent positive electromagnetic beads-production date", a concentration was calculated, and the aqueous dispersion was prepared into a 10 mg/mL dispersion; the dispersion was stored according to different categories in a refrigerator at 4 °C in the dark.

Example 3 Preparation of Plasma Polymerization-Based PEI Positive Electromagnetic Beads (1) Preparation of APS-FITC 1.5 mg of FITC dye was dissolved in 0.5 mL of absolute ethanol in a 1.5 mL centrifuge tube. The resulting FITC solution was transferred into a small glass reaction vial, diluted with 2 mL of absolute ethanol, and magnetically stirred for 1 min to mix well. 5 μL of APS was added into the resulting diluted solution, the reaction system immediately turned orange, and then magnetically stirred overnight until a product became a clear solution, thereby obtaining an APS-FITC solution, where the experiment was conducted always in the dark.

(2) Preparation of Fluorescent Negative Electromagnetic Beads by Fluorescence Labeling and TEOS Coating 0.7 mL of ammonia water was added into a mixture of 45 mL of absolute ethanol and 5 mL of deionized water, and mechanically stirred to mix well. 30 mg of $Fe_3O_4@SiO_2$ prepared according to Example 1 was added and stirred under ultrasound for about 30 min to obtain a uniform dispersion. 30 μL of TEOS was dissolved in 1 mL of absolute ethanol, and added into the above dispersion slowly dropwise under ultrasound and mechanical stirring to obtain a reaction system. The reaction system was stirred under ultrasound for another 15 min, then an APS-FITC solution was quickly added into the reaction system, and mechanically stirred under ultrasound for another 4 h in the dark. Then the ultrasound was stopped, the reaction system was mechanically stirred for 18 h, and a product was obtained under the assistance of magnetic separation and washed three times with ethanol and deionized water separately, obtaining the fluorescent negative electromagnetic beads, which were marked as "fluorescent negative electromagnetic beads-production date", a concentration was calculated and marked, and the beads were prepared into a 10 mg/mL dispersion, which was stored according to different categories in a refrigerator at 4 °C in the dark.

(3) Preparation of PEI-Modified Fluorescent Positive Electromagnetic Beads 18 mg of a fluorescent negative electromagnetic bead powder was added into a plasma reaction chamber, and overall air tightness of the plasma reaction chamber was checked. A mechanical pump was started to vacuumize the chamber to not more than 200 Pa, and an RF power supply was started to preheat for 15 min to 20 min. A nitrogen valve was opened, and nitrogen was introduced while the mechanical pump was running, such that a nitrogen pressure was stable at 300 Pa to 400 Pa. An RF device was started, an RF current and an RF voltage were adjusted to generate plasma glow in the reaction chamber, and the RF power was adjusted to stabilize at about 10 W. A reaction was conducted by heating to volatilize PEI (where 10 mg of PEI was dissolved in 2 mL of methanol and introduced into the plasma reaction chamber), and a monomer flow rate was adjusted to 3 sccm to 5 sccm through a flow meter. The reaction was conducted for 1 h to 2 h under stable conditions.

Example 4 Preparation of Chitosan Positive Electromagnetic Beads (1) Preparation of APS-FITC 1.5 mg of FITC dye was dissolved in 0.5 mL of absolute ethanol in a 1.5 mL centrifuge tube. The resulting FITC solution was transferred into a small glass reaction vial, diluted with 2 mL of absolute ethanol, and magnetically stirred for 1 min to mix well. 5 L of APS was added into the resulting diluted solution, the reaction system immediately turned orange, and then magnetically stirred overnight until a product became a clear solution, thereby obtaining an APS-FITC solution, where the experiment was conducted always in the dark.

(2) Preparation of Fluorescent Negative Electromagnetic Beads by Fluorescence Labeling and TEOS Coating 0.7 mL of ammonia water was added into a mixture of 45 mL of absolute ethanol and 5 mL of deionized water, and mechanically stirred to mix well. 30 mg of $Fe_3O_4@SiO_2$ prepared according to Example 1 was added and stirred under ultrasound for about 30 min to obtain a uniform dispersion. 30 μL of TEOS was dissolved in 1 mL of absolute ethanol, and added into the above dispersion slowly dropwise under ultrasound and mechanical stirring to obtain a reaction system. The reaction system was stirred under ultrasound for another 15 min, then an APS-FITC solution was quickly added into the reaction system, and mechanically stirred under ultrasound for another 4 h in the dark. Then the ultrasound was stopped, the reaction system was mechanically stirred for 18 h, and a product was obtained under the assistance of magnetic separation and washed three times with the ethanol and deionized water separately, obtaining the fluorescent negative electromagnetic beads, which were marked as "fluorescent negative electromagnetic beads-production date", a concentration was calculated and marked, and the beads were prepared into a 10 mg/mL dispersion, which was stored according to different categories in a refrigerator at 4 °C in the dark.

(3) Preparation of Chitosan-Modified Fluorescent Positive Electromagnetic Beads 25 mL of methanol was added to 18 mg of the fluorescent negative electromagnetic beads obtained in the previous step, and mechanically stirred under ultrasound for 10 min in the dark until a mixture is uniform to obtain a reaction solution. 10 mg of β-chitosan was dissolved in 2 mL of methanol, added to the above reaction solution, stirred under ultrasound for 2 h. The resulting solution was subjected to magnetical separation to obtain a product, which was washed once with methanol and three times with water. Sample treatment: an obtained aqueous dispersion was marked as "fluorescent positive electromagnetic beads-production date", a concentration was calculated, and the aqueous dispersion was prepared into a 10 mg/mL dispersion; the dispersion was stored according to different categories in a refrigerator at 4 °C in the dark.

Example 5 Preparation of Plasma Polymerization-Based Chitosan Positive Electromagnetic Beads (1) Preparation of APS-FITC 1.5 mg of FITC dye was dissolved in 0.5 mL of absolute ethanol in a 1.5 mL centrifuge tube. The resulting FITC solution was transferred into a small glass reaction vial, diluted with 2 mL of absolute ethanol, and magnetically stirred for 1 min to mix well. 5 μL of APS was added into the resulting diluted solution, the reaction system immediately turned orange, and then magnetically stirred overnight until a product became a clear solution, thereby obtaining an APS-FITC solution, where the experiment was conducted always in the dark.

(2) Preparation of Fluorescent Negative Electromagnetic Beads by Fluorescence Labeling and TEOS Coating 0.7 mL of ammonia water was added into a mixture of 45 mL of absolute ethanol and 5 mL of deionized water, and mechanically stirred to mix well. 30 mg of $Fe_3O_4@SiO_2$ prepared according to Example 1 was added and stirred under ultrasound for about 30 min to obtain a uniform dispersion. 30 μL of TEOS was dissolved in 1 mL of absolute ethanol, and added into the above dispersion slowly dropwise under ultrasound and mechanical stirring to obtain a reaction system. The reaction system was stirred under ultrasound for another 15 min, then an APS-FITC solution was quickly added into the reaction system, and mechanically stirred under ultrasound for another 4 h in the dark. Then the ultrasound was stopped, the reaction system was mechanically stirred for 18 h, and a product was obtained under the assistance of magnetic separation and washed three times with ethanol and deionized water separately, obtaining the fluorescent negative electromagnetic beads, which were marked as "fluorescent negative electromagnetic beads-production date", a concentration was calculated and marked, and the beads were prepared into a 10 mg/mL dispersion, which was stored according to different categories in a refrigerator at 4 °C in the dark.

(3) Preparation of Chitosan-Modified Fluorescent Positive Electromagnetic Beads 18 mg of a fluorescent negative electromagnetic bead powder was added into a plasma reaction chamber, and overall air tightness of the plasma reaction chamber was checked. A mechanical pump was started to vacuumize the chamber to not more than 200 Pa, and an RF power supply was started to preheat for 15 min to 20 min. A nitrogen valve was opened, and nitrogen was introduced while the mechanical pump was running, such that a nitrogen pressure was stable at 300 Pa to 400 Pa. An RF device was started, an RF current and an RF voltage were adjusted to generate plasma glow in the reaction chamber, and the RF power was adjusted to stabilize at about 10 W. A reaction was conducted by heating to volatilize β-chitosan (where 10 mg of the β-chitosan was dissolved in 2 mL of methanol and introduced into the plasma reaction chamber), and a monomer flow rate was adjusted to 3 sccm to 5 sccm through a flow meter. The reaction was conducted for 1 h to 2 h under stable conditions.

Final sample treatment: an obtained aqueous dispersion was marked as "plasma polymerization-based chitosan-positive electromagnetic beads-production date", a concentration was calculated, and the aqueous dispersion was prepared into a 10 mg/mL dispersion; the dispersion was stored according to different categories in a refrigerator at 4 °C in the dark.

Example 6 Preparation of Polypyrrole Positive Electromagnetic Beads (1) Preparation of APS-FITC 1.5 mg of FITC dye was dissolved in 0.5 mL of absolute ethanol in a 1.5 mL centrifuge tube. The resulting solution was transferred into a small glass reaction vial, diluted with 2 mL of absolute ethanol, and magnetically stirred for 1 min to mix well. 5 μL of APS was added into the resulting diluted solution, the reaction system immediately turned orange, and then magnetically stirred overnight until a product became a clear solution, thereby obtaining an APS-FITC solution, where the experiment was conducted always in the dark.

(2) Preparation of Fluorescent Negative Electromagnetic Beads by Fluorescence Labeling and TEOS Coating 0.7 mL of ammonia water was added into a mixture of 45 mL of absolute ethanol and 5 mL of deionized water, and mechanically stirred to mix well. 30 mg of $Fe_3O_4@SiO_2$ prepared according to Example 1 was added and stirred under ultrasound for about 30 min to obtain a uniform dispersion. 30 μL of TEOS was dissolved in 1 mL of absolute ethanol, and added into the above dispersion slowly dropwise under ultrasound and mechanical stirring to obtain a reaction system. The reaction system was stirred under ultrasound for another 15 min, then an APS-FITC solution was quickly added to the reaction system, and mechanically stirred under ultrasound for another 4 h in the dark. The ultrasound was stopped, the reaction system was mechanically stirred for 18 h, and a product was obtained under the assistance of magnetic separation and washed three times with ethanol and deionized water separately, obtaining the fluorescent negative electromagnetic beads, which were marked as "fluorescent negative electromagnetic beads-production date", a concentration was calculated and marked, and the beads were prepared into a 10 mg/mL dispersion, which was stored according to different categories in a refrigerator at 4 °C in the dark.

(3) Preparation of Polypyrrole-Modified Fluorescent Positive Electromagnetic Beads 25 mL of methanol was added into 18 mg of the fluorescent negative electromagnetic beads obtained in the previous step, and mechanically stirred under ultrasound for 10 min in the dark until a mixture is uniform to obtain a reaction solution. 10 mg of polypyrrole was dissolved in 2 mL of methanol, added to the above reaction solution, stirred under ultrasound for 2 h. The resulting solution was subjected to magnetical separation to obtain a product, which was washed once with methanol and three times with water. Sample treatment: an obtained aqueous dispersion was marked as "fluorescent positive electromagnetic beads-production date", a concentration was calculated, and the aqueous dispersion was prepared into a 10 mg/mL dispersion; the dispersion was stored according to different categories in a refrigerator at 4 °C in the dark.

Example 7 Preparation of Plasma Polymerization-Based Polypyrrole Positive Electromagnetic Beads (1) Preparation of APS-FITC 1.5 mg of FITC dye was dissolved in 0.5 mL of absolute ethanol in a 1.5 mL centrifuge tube. The resulting solution was transferred into a small glass reaction vial, diluted with 2 mL of absolute ethanol, and magnetically stirred for 1 min to mix well. 5 μL of APS was added into the resulting diluted solution, the reaction system immediately turned orange, and then magnetically stirred overnight until a product became a clear solution, thereby obtaining an APS-FITC solution, where the experiment was conducted always in the dark.

(2) Preparation of Fluorescent Negative Electromagnetic Beads by Fluorescence Labeling and TEOS Coating 0.7 mL of ammonia water was added into a mixture of 45 mL of absolute ethanol and 5 mL of deionized water, and mechanically stirred to mix well. 30 mg of $Fe_3O_4@SiO_2$ prepared according to Example 1 was added and stirred under ultrasound for about 30 min to obtain a uniform dispersion. 30 μL of TEOS was dissolved in 1 mL of absolute ethanol, and added into the above dispersion slowly dropwise under ultrasound and mechanical stirring to obtain a reaction system. The reaction system was stirred under ultrasound for another 15 min, then an APS-FITC solution was quickly added into the reaction system, and mechanically stirred under ultrasound for another 4 h in the dark. Then the ultrasound was stopped, the reaction system was mechanically stirred for 18 h, and a product was obtained under the assistance of magnetic separation and washed three times with the ethanol and deionized water separately, obtaining the fluorescent negative electromagnetic beads, which were marked as "fluorescent negative electromagnetic beads-production date", a concentration was calculated and marked, and the beads were prepared into a 10 mg/mL dispersion, which was stored according to different categories in a refrigerator at 4 °C in the dark.

(3) Preparation of Polypyrrole-Modified Fluorescent Positive Electromagnetic Beads 18 mg of a fluorescent negative electromagnetic bead powder was added into a plasma reaction chamber, and overall air tightness of the plasma reaction chamber was checked. A mechanical pump was started to vacuumize the chamber to not more than 200 Pa, and an RF power supply was started to preheat for 15 min to 20 min. A nitrogen valve was opened, and nitrogen was introduced while the mechanical pump was running, such that a nitrogen pressure was stable at 300 Pa to 400 Pa. An RF device was started, an RF current and an RF voltage were adjusted to generate plasma glow in the reaction chamber, and the RF power was adjusted to stabilize at about 10 W. A reaction was conducted by heating to volatilize polypyrrole (where 10 mg of the polypyrrole was dissolved in 2 mL of methanol and introduced into the plasma reaction chamber), and a monomer flow rate was adjusted to 3 sccm to 5 sccm through a flow meter. The reaction was conducted for 1 h to 2 h under stable conditions.

Effect Example 1 Performance of Multifunctional MNM

The multifunctional MNMs prepared according to Examples 1 to 7 were dispersed in an aqueous solution to observe their dispersibility. A magnet was placed at one side of a sample bottle containing the prepared MNMs, and the magnetic properties of the material were roughly determined through the attraction of the magnetic field to the materials. The hydrated particle size and surface potential of the materials were determined by using a laser particle size analyzer Zetasizer Nano-ZS (Malvern, UK). The particle size distribution of nanoparticles and the surface potential of nanoparticles were determined by a dynamic light scattering method. The morphology of nanoparticles was observed and analysed by a TEM. The fluorescence emission of the prepared MNMs was determined with a fluorescence spectrophotometer.

(1) Zeta Potential and Fluorescence Analysis of Multifunctional MNM

Figure 1B:
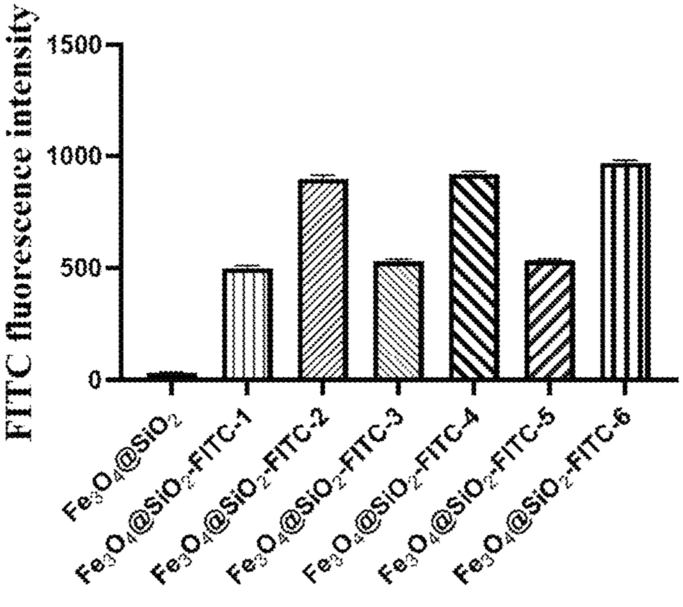

The potential characterization and fluorescence spectra of various $Fe_3O_4$ nanomaterials according to Examples 1 to 7 are shown in FIGS. 1A and 1B.

(2) Effect of Solution pH on the Zeta Potential of Nanomaterials

Figure 2:
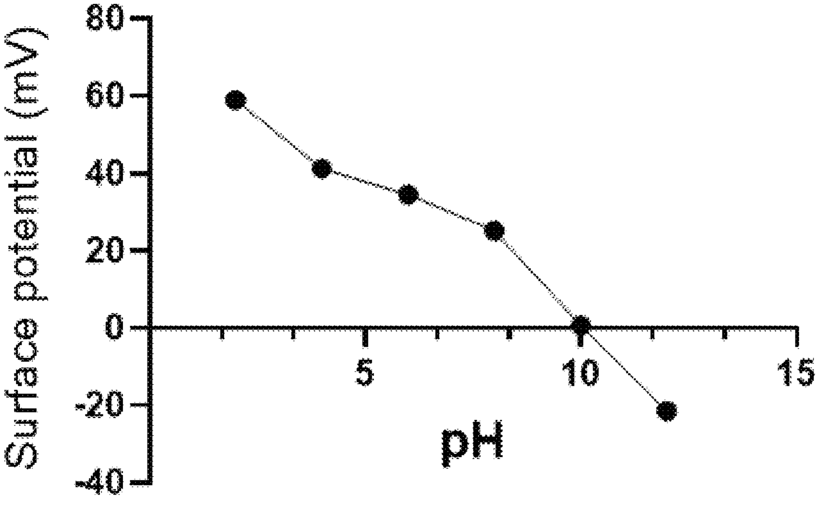
FIG. 2 shows the relationship between the potential and the pH of plasma polymerization-based PEI positive electromagnetic beads according to Example 3.

FIG. 2 shows a relationship between the potential and pH of plasma polymerization-based PEI positive electromagnetic beads according to Example 3.

(3) Observation of the Dispersion and Magnetic Properties of MNM in Solution

Figure 3A:
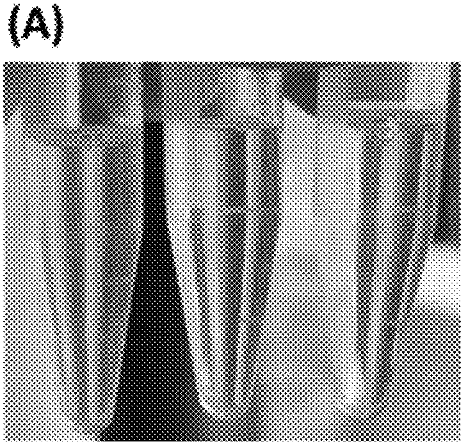
FIGS. 3A and 3B show photos of the plasma polymerization-based positive electromagnetic beads before and after magnetic separation according to Example 3, where
Figure 3B:
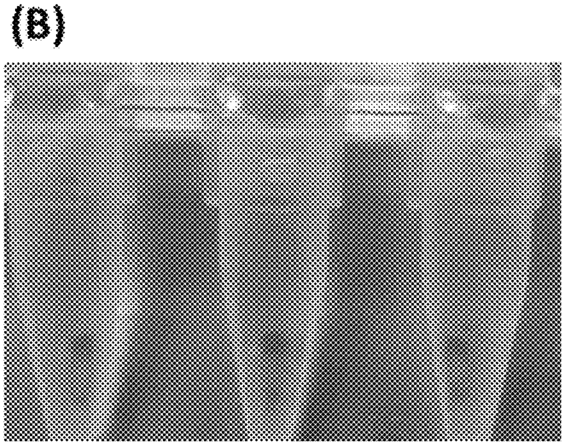

FIGS. 3A and 3B show photos of the plasma polymerization-based positive electromagnetic beads before and after magnetic separation according to Example 3, where FIG. 3A represents before the magnetic separation, FIG. 3B represents after the magnetic separation.

(4) Electron Microscopy of Nanomaterials

Figure 4:
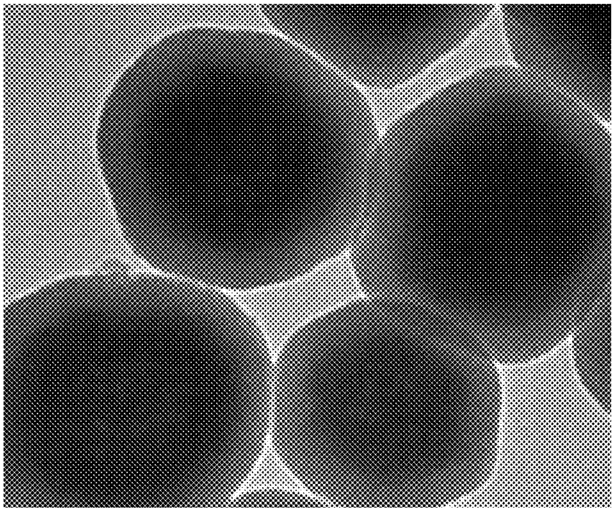
FIG. 4 shows a transmission electron microscopy (TEM) image of magnetic particles modified with PEI by plasma polymerization according to Example 3.

FIG. 4 shows a TEM image of magnetic particles modified with PEI by plasma polymerization according to Example 3.

Effect Example 2 Comparison of Non-Plasma Polymerization and Plasma Polymerization (1) Material Stability: Comparison of Potential (A) and Particle Size (B)

Figure 5A:
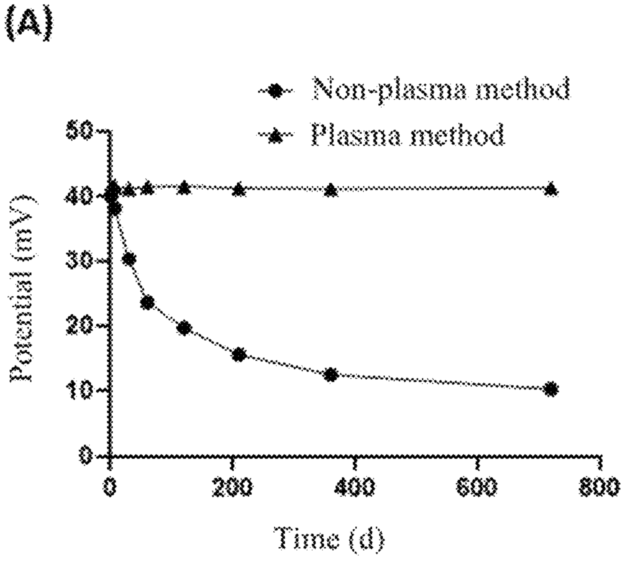
FIGS. 5A and 5B show stability comparison of materials according to Examples 2 and 3, where
Figure 5B:
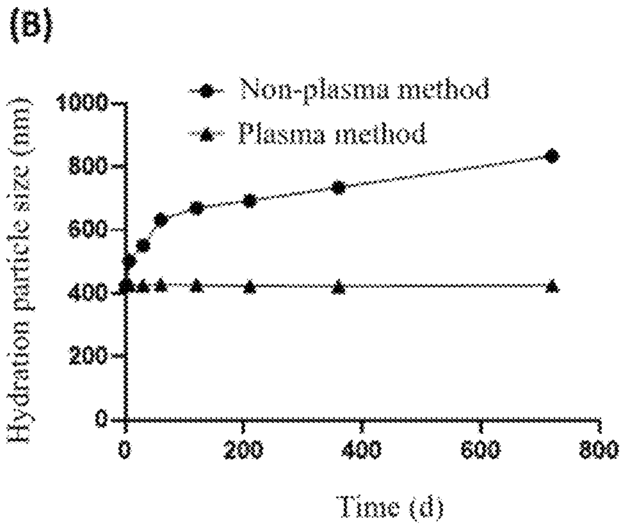

The stabilities of the materials according to Example 2 and Example 3 were compared, as shown in FIGS. 5A and 5B. The comparison of potential (A) shows that the potential of the material according to Example 2 declined significantly with time, from 40 to about 15 at 200 days. The potential of the material obtained according to Example 3 could remain unchanged for 2 years, and is significantly better than that of Example 2. In the comparison of particle size (B), the hydrated particle size of the material obtained according to Example 3 could remain unchanged for 2 years, and is significantly better than that of Example 2.

Figure 6:
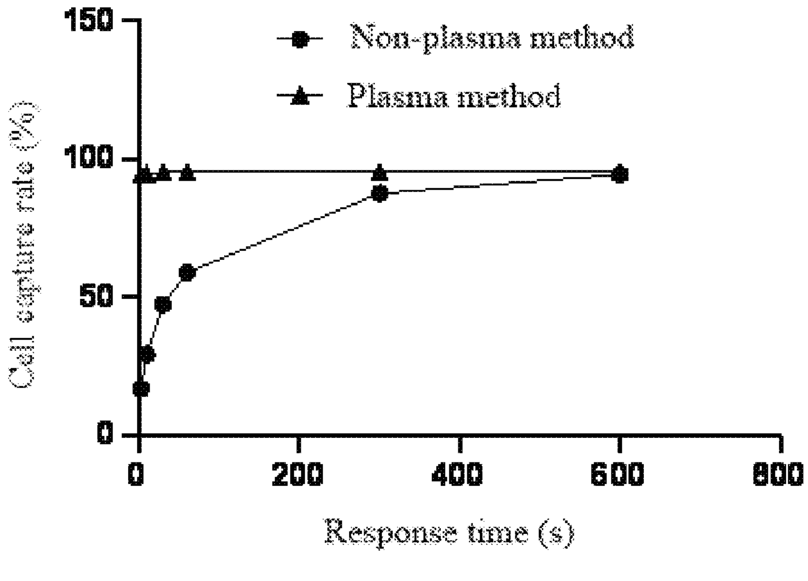
FIG. 6 shows response performance comparison of the materials according to Examples 2 and 3, namely comparison of a recovery rate in capturing CTCs at different times.

(2) Response Performance: Comparison of a Recovery Rate of CTC Captured at Different Times The comparison of a recovery rate of CTC captured by the materials of Example 2 and Example 3 at different times is shown in FIG. 6.

A response time of the material according to Example 3 produced by the plasma polymerization of the present disclosure could reach 3 seconds, which is significantly shorter than that obtained by the conventional non-plasma polymerization.

(3) Comparison of Graft Percentages of Polymers

Figure 7:
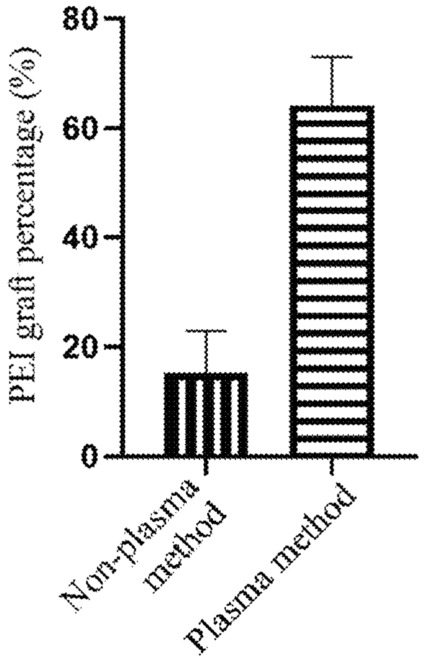
FIG. 7 shows comparison of a polymer graft modification percentage of the materials according to Examples 2 and 3.

The comparison of the grafting percentages of the polymers of the materials according to Example 2 and Example 3 is shown in FIG. 7.

A ratio of a mass of the polymer to a feeding amount in the polymer-modified MNM according to Example 3 could reach not less than 60%.

A ratio of a mass of the polymer to a feeding amount in the polymer-modified MNM according to Example 2 is only about 15%.

Compared with Examples 4 and 6, Examples 5 and 7 could obtain similar effects.

Use Example 1

Figure 8:
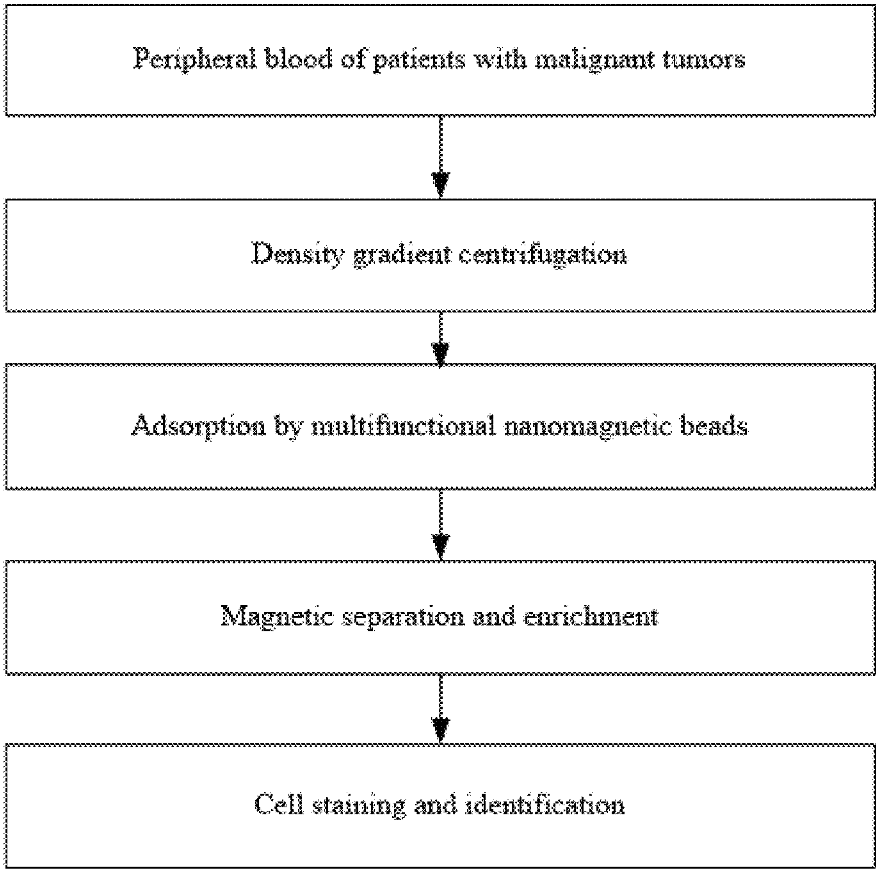
FIG. 8 is a schematic diagram that shows a detection process of the CTCs according to Use Example 1.

Use of the polymer-modified MNM was provided in preparation of a drug or reagent for capturing CTCs. As shown in FIG. 8, the use was specifically conducted as follows:

(1) 4 mL of a peripheral blood sample was collected;

(2) a density gradient separation medium (Percoll cell separation medium) was slowly added into a 15 mL centrifuge tube in a layered manner sequentially;

(3) the peripheral blood sample was mixed to be uniform, and 1 mL of the peripheral blood sample was diluted 3 to 4 times with PBS;

(4) the diluted peripheral blood sample was slowly added into the centrifuge tube containing the gradient separation medium, and centrifuged at 1,600 r for 30 min;

(5) after the centrifugation was completed, an obtained white blood cell layer was placed in a 15 mL centrifuge tube, the cells were resuspended with 4 mL to 6 mL of PBS, and centrifuged at 1,600 r for 7 min;

(6) after the centrifugation was completed, a supernatant was removed, the cells were resuspended with 1 mL of PBS, and transferred into a 1.5 mL centrifuge tube;

(7) a drug or reagent (PEI-coated MNP according to Example 3) was activated by ultrasound, and 30 μL of the drug or reagent was added to the 1.5 mL centrifuge tube, and then placed on a mini rotary incubator and incubated at 4 °C and 4 rpm/min for 10 min;

(8) after the incubation was completed, the centrifuge tube was inserted into a multifunctional magnetic separator and subjected to magnetic adsorption at 4 °C for 10 min;

(9) a resulting supernatant was removed, the remaining substance was mixed well with 1 mL of PBS, and the centrifuge tube was inserted into the multifunctional magnetic separator and subjected to magnetic adsorption at 4 °C for 10 min;

(10) a resulting supernatant was removed, the remaining substance was resuspended and mixed to be uniform in 200 μL of PBS, and subjected to cytospin to obtain 1 to 2 slides;

(11) the slide was stained with Diff-Quik Stain; and

(12) the cells were determined and counted under an optical microscope.

Figure 10:
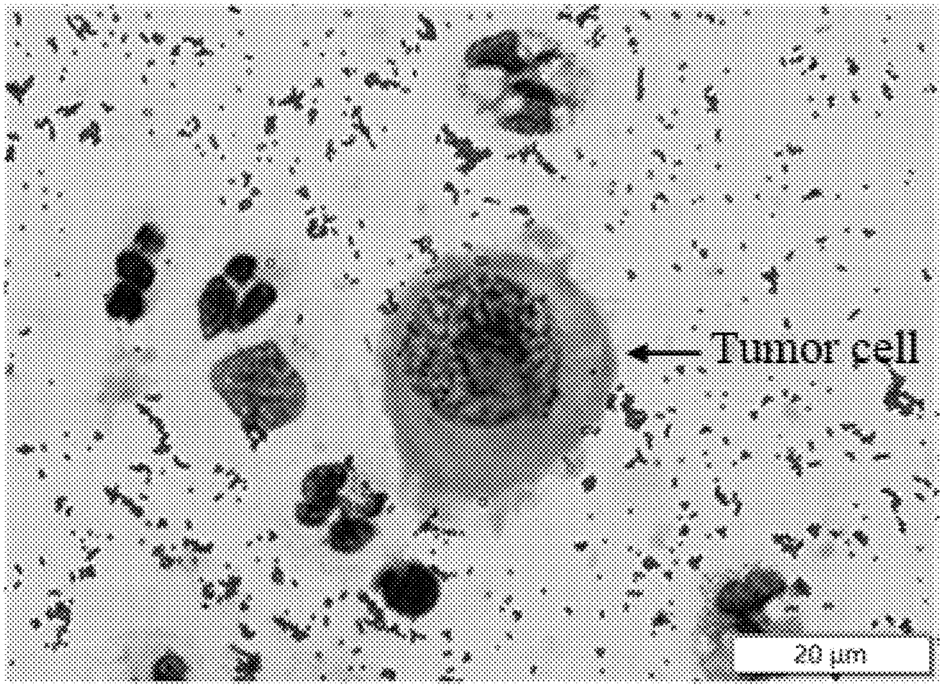
FIG. 10 shows a photograph of an optical microscope of tumor cells according to Use Example 1.

As shown in FIG. 10: the cells have large volume, high nuclear-to-cytoplasmic ratio, and different nuclear shapes, showing meganuclear, dual-nucleated, or multi-nucleated state; the nuclei were hyperchromatic and unevenly stained; fat granules were common in the cytoplasm; and the cell membrane had surface folds or well-defined borders. The above are the morphological characteristics of tumor cells, and cells that meet the above four or more characteristics are determined to be tumor cells.

Compared with the commercially available Johnson & Johnson CellSearch product, this example only required 4 mL of peripheral blood, and the detection was completed within 2 h; however, the Johnson & Johnson CellSearch technology required 7.5 mL of peripheral blood, and the detection took at least 6 h.

Figure 11A:
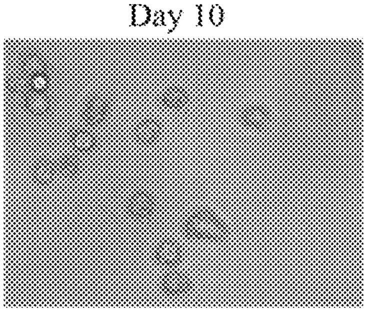
FIGS. 11A, 11B, and 11C show results of captured CTCs after culturing for 10 days, 20 days, and 30 days according to Use Example 1.
Figure 11B:
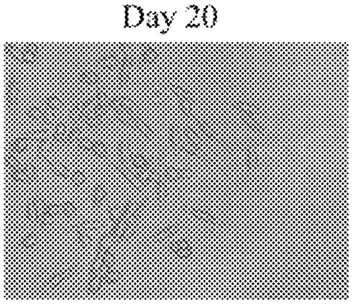
Figure 11C:
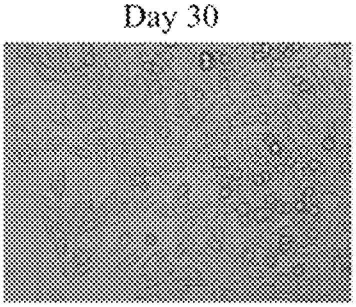

As shown in FIGS. 11A-11C, by culturing the captured CTCs, it could be seen that there is obvious proliferation after 10 days, 20 days, and 30 days of culture, indicating that the captured CTCs are living cells.

Use Example 2

158 cases of healthy volunteers and 853 cases of malignant tumor volunteers were detected by a use method of Use Example 1. The patients diagnosed in Quanzhou First Hospital from January 2020 to December 2021 were collected as follows: 215 patients with colon cancer, aged 34-86 years, 149 males and 66 females; 188 patients with lung cancer, aged 32-85 years, 113 males and 75 females; 145 patients with rectal cancer, aged 42-78 years, 104 males and 41 females; 94 patients with gastric cancer, aged 30-87 years, 61 males and 33 females; 86 patients with breast cancer, aged 33-74 years, 1 male and 85 females; 74 patients with esophageal cancer, aged 51-82 years, 55 males and 19 females; and 51 patients with liver cancer, aged 43-76 years, 40 males and 11 females. A total of the 158 healthy subjects who underwent physical examination in this hospital during the same period were selected as healthy controls, aged 22-75 years, 101 males and 57 females.

The selection criteria for volunteers in this use example were as follows:

1. Inclusion criteria:

1.1 Malignant tumor volunteers a. Subjects over 18 years old (including 18 years old), regardless of gender.

b. Patients with a single malignant tumor of colon cancer, lung cancer, rectal cancer, gastric cancer, breast cancer, esophageal cancer, and liver cancer confirmed by imaging and pathology.

c. Patients who were still undergoing radiotherapy and chemotherapy, immunotherapy, or targeted therapy.

1.2 Healthy volunteers a. Subjects over 18 years old (including 18 years old), regardless of gender.

b. Subjects with normal results in blood or urine routine examination.

2. Exclusion criteria:

2.1 Malignant tumor volunteers a. Patients with malignant tumors having other complications.

b. In addition to colon cancer/lung cancer/rectal cancer/gastric cancer/breast cancer/esophageal cancer/liver cancer, patients with previous history of other malignant tumors.

2.2 Healthy volunteers a. Subjects taking drugs for a long time;

b. Subjects with family history of chronic diseases or tumors;

c. Subjects with nodules or suspected tumors found in physical examination.

Figure 9:
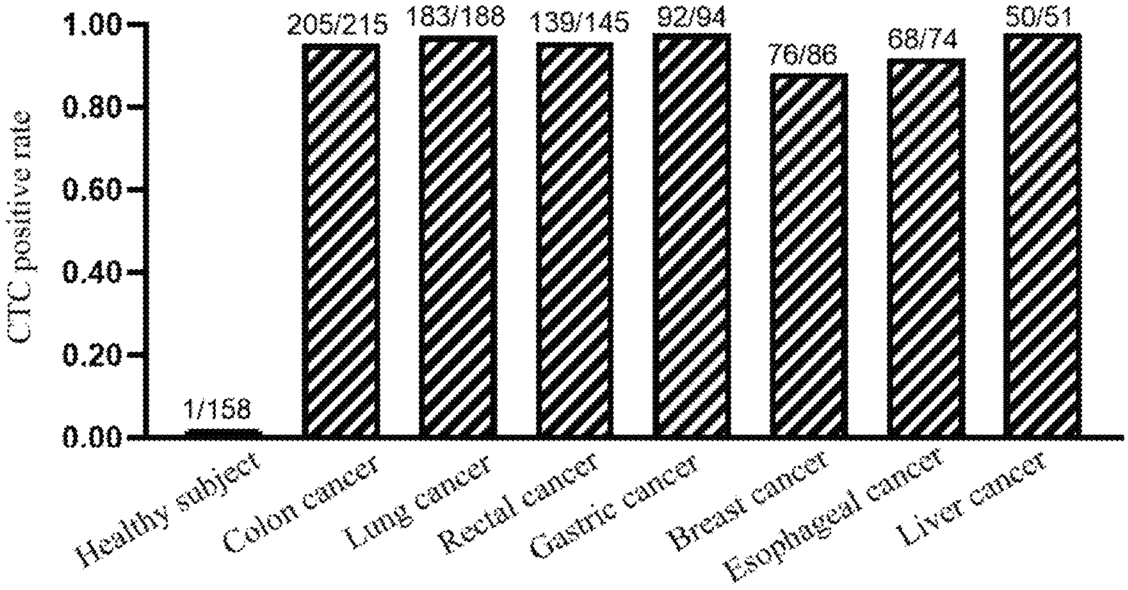
FIG. 9 shows comparison of a detection rate of normal people and malignant tumor patients according to Use Example 2.

The results are shown in FIG. 9, where only 1 case is detected in the 158 cases of the healthy control group, and a false positive rate is extremely low, only 0.6%; in the 215-case colon cancer group, 205 cases are detected, with a detection rate of 95.3%; in the 188-case lung cancer group, 183 cases are detected, with a detection rate of 97.3%; in the 145-case rectal cancer group, 139 cases are detected, with a detection rate of 95.9%; in the 94-case gastric cancer group, 92 cases are detected, with a detection rate of 97.9%; in the 86-case breast cancer group, 76 cases are detected, with a detection rate of 88.4%; in the 74-case esophageal cancer group, 68 cases are detected, with a detection rate of 91.9%; in the 51-case liver cancer group, 50 cases are detected, with a detection rate of 98%.

What is claimed is:

1. A method for preparing a polymer-modified magnetic nanomaterial (MNM), comprising the following steps:

subjecting an MNM and a mixture of a polymer and a solvent to modification by a plasma method to obtain the polymer-modified MNM, wherein the mixture of the polymer and the solvent is in an atomized form; wherein the polymer is a cationic polymer;

the polymer is attached to or coated on a surface of the MNM to form the polymer-modified MNM that is positively charged;

the MNM has a core-shell structure, a core is a magnetic nanoparticle (MNP), a shell is a modified layer, and the modified layer is attached to or coated on a surface of the MNP to form a modified layer-compounded MNP; and a mass ratio of the polymer to the MNM in the polymer-modified MNM is in a range of 1:10 to 20:1.

2. The method of claim 1, wherein the method satisfies at least one of the following conditions:

(1) the solvent is methanol, (2) a ratio of a mass of the polymer to a volume of the mixture is 5 mg:1 mL, (3) the mixture of the polymer and the solvent is added at a monomer flow rate of 3 sccm to 5 sccm, (4) the modification is conducted at a temperature of 100 °C to 300 °C, (5) the modification is conducted in an inert atmosphere, and the inert atmosphere is provided by nitrogen and/or argon, (6) the modification is conducted for 1 h to 2 h; and (7) when the MNM is the silica-compounded MNP or the fluorescently-labeled silica-compounded MNP, and the silica-compounded MNP is the $Fe_3O_4$@$SiO_2$, the MNM is prepared by a process comprising the following steps:

step (a), in the presence of an alkaline reagent, adding a silicon reagent into a system of the $Fe_3O_4$ MNP and a solvent, and conducting modification to obtain the $Fe_3O_4$@$SiO_2$; and/or step (b), subjecting the $Fe_3O_4$@$SiO_2$ and the fluorescent dye to fluorescent labeling reaction to obtain the fluorescently-labeled silica-compounded MNP.

3. The method of claim 2, wherein the process for preparing the MNM satisfies at least one of the following conditions:

(1) the method for preparing the polymer-modified MNM comprises the following steps: under the inert atmosphere and in the presence of plasma glow, heating the mixture of the polymer and the solvent to obtain the atomized form, and subjecting the mixture in the atomized form to the modification with the MNM to obtain the polymer-modified MNM, wherein the plasma glow is obtained by the following steps: in the inert atmosphere, adjusting a radio frequency power to generate the plasma glow in a plasma reaction chamber, wherein the inert atmosphere has a pressure of 300 Pa to 400 Pa, the radio frequency power is 10 W±5 W, a radio frequency power supply is preheated under vacuum, and then the inert atmosphere is introduced into the plasma reaction chamber, the vacuum having a vacuum degree of 150 Pa to 200 Pa, (2) the solvent in step (a) is selected from the group consisting of water and a mixture of water and ethanol, (3) the alkaline reagent is aqueous ammonia, (4) the silicon reagent is tetraethyl orthosilicate (TEOS) or tetramethyl orthosilicate (TMOS), (5) a ratio of a mass of the $Fe_3O_4$ MNP to a volume of the silicon reagent is 1 L 1500 g:1 L, (6) the silicon reagent is used in a mixture with the solvent, (7) the alkaline reagent is added in such an amount that the system of the $Fe_3O_4$ MNP and the solvent has a pH value of 9.5±0.5, (8) the modification is conducted under ultrasound and/or mechanical stirring, (9) the method further comprises post-treatment in step (a), and the post-treatment comprises: after the modification is completed, washing the $Fe_3O_4@SiO_2$ obtained with assistance of magnetic separation, the washing being conducted with ethanol and deionized water separately three times; after the washing is completed, the $Fe_3O_4@SiO_2$ is dispersed in deionized water to prepare a solution with a concentration of 100 mg/mL for later use,

(10) in step (b), the solvent is a mixture of ethanol and deionized water, and a volume ratio of the ethanol to the deionized water is in a range of 9:1 to 10:1,

(11) in step (b), a ratio of a mass of the silica-compounded MNP to a volume of the solvent is in a range of (0.56-0.6) g:1 L,

(12) in step (b), the alkaline reagent is aqueous ammonia, and a ratio of a mass of the silica-compounded MNP to a volume of the aqueous ammonia is in a range of (42-45) g:1 L,

(13) in step (b), the fluorescent dye is used in a mixture with the solvent, and a ratio of a volume of the solvent to a mass of the fluorescent dye is 1.7 mL: 1 mg,

(14) the fluorescent labeling reaction is conducted under ultrasound and mechanical stirring,

(15) the fluorescent labeling reaction is conducted in the dark,

(16) the method further comprises, in step (b), adding the silicon reagent as defined in step (a) into the fluorescent labeling reaction, that is, further coating the silica, wherein a ratio of a mass of the silica-compounded MNP to a volume of the silicon reagent is 1000 g: 1 L, the silicon reagent is in a form of a mixture with the solvent;

(17) the method further comprises post-treatment in step (b), and the post-treatment comprises: after the fluorescent labeling reaction is completed, washing the MNP obtained with assistance of magnetic separation, the washing being conducted with ethanol and deionized water separately three times,

(18) when the fluorescent dye is the APS-FITC, the APS-FITC is prepared by a process comprising: adding APS into a solution of FITC in ethanol, and conducting reaction to obtain the APS-FITC, wherein the reaction is conducted in the dark, the reaction is conducted until a clear solution is obtained, by mixing overnight, and a ratio of a mass of the FITC to a volume of the APS is 300 g:1 L,

(19) in step (a), the system of the $Fe_3O_4$ MNP and the solvent is prepared by a process comprising: under ultrasound and mechanical stirring, washing $Fe_3O_4$ nano magnetic beads in the solvent with hydrochloric acid and deionized water successively until a resulting supernatant has a neutral pH value, wherein the hydrochloric acid has a concentration of 3.6% to 36%; and

(20) in step (a), when the MNP in the MNM is $Fe_3O_4$, the MNP is prepared by a process comprising: subjecting $FeCl_3 \cdot 6H_2O$ and a solution of an alkali metal salt in ethylene glycol to reaction to obtain the $Fe_3O_4$ MNPs, wherein the alkali metal salt is selected from the group consisting of trisodium citrate and sodium acetate (NaAc), a molar ratio of $FeCl_3 \cdot 6H_2O$ to NaAc is 1:10, a ratio of a volume of the solvent to a molar number of $FeCl_3 \cdot 6H_2O$ is 10 L:1 mol, and the reaction is conducted at 200 °C; the process further comprises post-treatment, and the post-treatment comprises the following steps: after the reaction is finished, washing the $Fe_3O_4$ MNP obtained with assistance of magnetic separation, wherein the washing is conducted with ethanol and deionized water separately three times; after the washing is completed, the $Fe_3O_4$ MNP is dispersed in deionized water to prepare a solution with a concentration of 100 mg/mL for later use.

4. The method of claim 1, wherein the polymer-modified MNM satisfies at least one of the following conditions:

(1) the mass ratio of the polymer to the MNM is in a range of 1:5 to 3:1, (2) the polymer-modified MNM has a zeta potential of +5 mV to +60 mV, (3) the MNM is a negatively-charged MNM, with a zeta potential of −10 mV to −60 mV, (4) the polymer-modified MNM has a particle size of 10 nm to 600 nm, (5) the MNM has a particle size of 5 nm to 500 nm, (6) the shell has a thickness of 1 nm to 100 nm, (7) the MNP has a particle size of 5 nm to 500 nm, (8) the polymer is one or more selected from the group consisting of polyethyleneimine, chitosan, and polypyrrole, (9) the polymer is a branched polymer,

(10) the polymer has a weight-average molecular weight (MW) of 2,000 to 300,000,

(11) the MNP is one or more selected from the group consisting of an oxide MNP, a metal MNP, a sulfide MNP, and a magnetic composite particle, and the oxide MNP is selected from the group consisting of an $Fe_3O_4$ MNP and a $\gamma$-$Fe_2O_3$ MNP,

(12) the modified layer is prepared from silica or fluorescently-labeled and/or surfactant-modified silica,

(13) a surface of the modified layer has an amino group obtained by modification,

(14) a mass ratio of the modified layer to the MNP is in a range of 50:1 to 1:10,

(15) the polymer-modified MNM has a stable duration of 2 years, and

(16) the polymer-modified MNM has a response time of 3 seconds.

5. The method of claim 4, wherein the polymer-modified MNM satisfies at least one of the following conditions:

(1) when the polymer is the polyethyleneimine, the polyethyleneimine has an MW of 2,000 to 100,000, and a purity of 99%, (2) when the polymer is β-chitosan, the β-chitosan has an MW of 50,000 to 300,000, (3) when the polymer is the polypyrrole, the polypyrrole has an MW of 5,000, (4) when the MNM is a fluorescently-labeled silica-compounded MNP, a fluorescent dye in the fluorescently-labeled silica-compounded MNP is fluorescein isothiocyanate (FITC) and/or a rhodamine dye, and/or a modified substance thereof, the modified substance is APS-modified FITC and/or an APS-modified rhodamine dye, and APS is 3-aminopropyltriethoxysilane and/or 3-aminopropyltrimethylsilane, (5) the MNM is a surfactant-modified silica-compounded MNP; and a surfactant is one or a combination of two or more selected from the group consisting of sodium acetate, trisodium citrate, chitosan, polyvinylpyrrolidone, polyethylene terephthalate, stearic acid, gum arabic, hydroxypropyl methylcellulose, sodium alginate, lauryl sodium sulfate, sodium dodecylbenzene sulfonate, polyvinyl alcohol, a long-chain fatty acid, starch, and dodecanethiol, (6) when the MNM is the fluorescently-labeled silica-compounded MNP, a mass ratio of the silica-compounded MNP to the fluorescent dye is 20:1, (7) when the MNM is the fluorescently-labeled silica-compounded MNP, the polymer-modified MNM has a fluorescence intensity of 40 to 1,200, (8) when the MNM is a silica modified layer-compounded MNP, the silica modified layer-compounded MNP is an $Fe_3O_4$@$SiO_2$, and (9) when the MNM is a fluorescently-labeled silica modified layer-compounded MNP, the fluorescently-labeled silica modified layer-compounded MNP is an APS-FITC-labeled $Fe_3O_4$@$SiO_2$.

6. The method of claim 1, wherein the polymer-modified MNM is one selected from the following schemes:

scheme 1:

the polymer-modified MNM is a polyethyleneimine-modified APS-FITC-fluorescently-labeled $Fe_3O_4$@$SiO_2$, wherein polyethyleneimine has an MW of 10,000, a mass ratio of the polyethyleneimine to the MNM is 1:3, and the polymer-modified MNM has a particle size of 20 nm to 500 nm and a zeta potential of +10 mV to +60 mV;

scheme 2:

the polymer-modified MNM is a β-chitosan-modified APS-FITC-fluorescently-labeled $Fe_3O_4$@$SiO_2$, wherein β-chitosan has an MW of 50,000, a mass ratio of the β-chitosan to the MNM is 1:3, and the polymer-modified MNM has a particle size of 20 nm to 500 nm and a zeta potential of +10 mV to +60 mV; and scheme 3:

the polymer-modified MNM is a polypyrrole-modified APS-FITC-fluorescently-labeled $Fe_3O_4$@$SiO_2$, wherein polypyrrole has an MW of 5,000, a mass ratio of the polypyrrole to the MNM is 1:3, and the polymer-modified MNM has a particle size of 20 nm to 500 nm and a zeta potential of +10 mV to +60 mV.

7. The method of claim 2, wherein the method satisfies the following condition:

the modification is conducted at 200 °C.

8. The method of claim 3, wherein the process for preparing the MNM satisfies at least one of the following conditions:

(1) the silicon reagent is TEOS, (2) the silicon reagent is used in a mixture of 100 μL of the TEOS dissolved in 2 mL of ethanol, (3) in step (b), the solvent is a mixture of ethanol and deionized water, and a volume ratio of the ethanol to the deionized water is 9.7:1, and (4) the method further comprises, in step (b), adding the silicon reagent as defined in step (a) into the fluorescent labeling reaction, that is, further coating the silica, wherein a ratio of a mass of the silica-compounded MNP to a volume of the silicon reagent is 1000 g:1 L, and the silicon reagent is a mixture of 30 μL of the TEOS in 1 mL of the ethanol.

9. The method of claim 4, wherein the polymer-modified MNM satisfies at least one of the following conditions:

(1) the mass ratio of the polymer to the MNM is 1:3, (2) the polymer-modified MNM has a zeta potential of +10 mV to +50 mV, (3) the MNM is a negatively-charged MNM, with a zeta potential of −20 mV to −40 mV, (4) the polymer-modified MNM has a particle size of 300 nm to 500 nm, (5) the MNM has a particle size of 300 nm to 350 nm, (6) the shell has a thickness of 40 nm to 60 nm, (7) the MNP has a particle size of 250 nm to 300 nm, (8) the MNP is one or more selected from the group consisting of an oxide MNP, a metal MNP, a sulfide MNP, and a magnetic composite particle, and the oxide MNP is an $Fe_3O_4$ MNP, (9) the modified layer is prepared from silica or fluorescently-labeled silica, and

(10) a mass ratio of the modified layer to the MNP is in a range of 1:2 to 10:1.

10. The method of claim 9, wherein the polymer-modified MNM satisfies at least one of the following conditions:

(1) the polymer-modified MNM has a potential of +20 mV to +40 mV, and (2) the polymer-modified MNM has a particle size of 350 nm to 400 nm.

11. The method of claim 5, wherein the polymer-modified MNM satisfies at least one of the following conditions:

(1) when the polymer is the polyethyleneimine, the polyethyleneimine has an MW of 10,000, and a purity of 99%, (2) when the polymer is β-chitosan, the β-chitosan has an MW of 50,000, and (3) when the MNM is a fluorescently-labeled silica-compounded MNP, a fluorescent dye in the fluorescently-labeled silica-compounded MNP is one or more selected from the group consisting of FITC, rhodamine B, rhodamine B 5-isothiocyanate, and tetramethylrhodamine isothiocyanate and/or APS-FITC.

* * * * *